United States Patent
Weyl et al.

[11] Patent Number: 6,032,514
[45] Date of Patent: Mar. 7, 2000

[54] GAS MEASURING SENSOR

[75] Inventors: Helmut Weyl, Schwieberdingen, Germany; Udo Jauernig, Yokohama, Japan

[73] Assignee: Robert Bosch GmbH, Stuttgart, Germany

[21] Appl. No.: 09/133,227

[22] Filed: Aug. 13, 1998

[30] Foreign Application Priority Data

Aug. 16, 1997 [DE] Germany ............................ 197 35 559

[51] Int. Cl.[7] ............................ G01N 27/04; G01N 27/46; H01C 7/00; H01L 7/00
[52] U.S. Cl. ........................ 73/31.05; 73/23.31; 73/23.32; 204/424; 338/34; 29/878
[58] Field of Search ..................... 73/31.05, 29.05, 73/23.32, 23.2, 23.31; 204/424; 338/34; 29/878

[56] References Cited

U.S. PATENT DOCUMENTS

| | | | |
|---|---|---|---|
| 4,260,978 | 4/1981 | Yasuda et al. | 338/34 |
| 4,308,518 | 12/1981 | Hattori et al. | 338/34 |
| 4,309,897 | 1/1982 | Springer et al. | 73/23 |
| 4,668,477 | 5/1987 | Nishio et al. | 422/98 |
| 5,039,972 | 8/1991 | Kato et al. | 338/34 |
| 5,329,806 | 7/1994 | McClanahan et al. | 73/31.05 |
| 5,546,787 | 8/1996 | Häfele et al. | 73/23.31 |
| 5,585,547 | 12/1996 | Kim et al. | 73/31.05 |
| 5,616,825 | 4/1997 | Achey et al. | 73/23.31 |
| 5,739,414 | 4/1998 | Paulus et al. | 73/23.31 |
| 5,755,941 | 5/1998 | Weyl | 204/424 |
| 5,874,663 | 2/1999 | Fukaya et al. | 73/23.32 |
| 5,880,353 | 3/1999 | Graser et al. | 73/23.2 |

FOREIGN PATENT DOCUMENTS 195 40 022  4/1997  Germany.

*Primary Examiner*—Hezron Williams
*Assistant Examiner*—J. David Wiggins
*Attorney, Agent, or Firm*—Kenyon & Kenyon

[57] ABSTRACT

A engine exhaust gas measuring sensor having a sealing device and having a sleeve suitable for connection to a housing including a sealing element which is arranged at an end of sleeve facing away from the housing so that a reference air chamber is formed within the sleeve. The sealing element also has at least one opening extending longitudinally and at least one oblong contact which penetrates the opening and serves the purpose of establishing an electrical bond with a sensor element of the lambda probe. A glass seal is placed within the opening for the purpose of sealing and insulation. The glass seal encloses a longitudinal section of the contact located within the opening in the form of a jacket. The sealing element and the sleeve are made of metal. A method for making such an engine exhaust gas sensor includes the steps of introducing solder glass in a sealing element opening, heating the solder glass so that it becomes fluid and cooling the glass so that is solidifies or sets.

12 Claims, 2 Drawing Sheets

GAS MEASURING SENSOR

FIELD OF THE INVENTION

The present invention relates to a gas measuring sensor having a sealing device and having a sleeve suitable for connection to a housing. The gas measuring sensor of the present invention also includes a sealing element which is arranged at the end of the sleeve facing away from the housing; the sealing element has at least one opening extending longitudinally as well as at least one oblong contact which penetrates the opening and serves the purpose of establishing an electrical bond with a sensor element arranged in the housing. In addition, the present invention relates to a method for manufacturing the sealing device.

BACKGROUND INFORMATION

Lambda probes which include a sealing device on the reference air side are well-known. In this type of lambda probe, a section of a sensor element is introduced into the exhaust air stream to be measured while another area of the sensor element is located in a so-called reference air chamber for the purpose of reference. This reference air chamber is formed by one part of the housing of the lambda probe and of the sealing device, the sealing device having the function of sealing the reference air chamber as tightly as possible.

German Published Patent Application No. 195 40 022 describes an arrangement for the sealing of a cable penetration for lambda probes of motor vehicles. The sealing takes place using a bushing which seals a housing of the lambda probe on one side. The electrical contact of the sensor element is established via cables which have an electrically conducting core and an insulating jacket and which penetrate the bushing. The bushing itself is made from glass fiber reinforced Teflon. In order to improve the seal, an O-ring is additionally inserted between the inside wall of the housing and the bushing.

This sealing arrangement is as much in need of improvement as its manufacture is expensive. Furthermore, the use of an insulating jacket for the cables causes problems in relation to a desired hermetic seal, particularly at high temperatures.

SUMMARY OF THE INVENTION

The gas measuring sensor according to the present invention has the advantage that easy assembly and manufacture are possible. In addition, high temperature resistance with simultaneous very good sealing are attainable. The fact that the sealing element inserted into the sleeve is made of metal and a vitreous material makes it possible to achieve a very high heat resistance, whereby the seal is not adversely affected. The sealing of openings intended for the penetration of the contacts is achieved by the introduction of a glass seal which furthermore provides for the thermal insulation from the sealing element which is made of metal. An additional advantage of the use of a sealing element of metal can be seen in the fact that a welded connection with the sleeve is possible, which in addition to fixation also assumes a sealing function.

In an advantageous embodiment of the present invention, the sealing element made of metal is arranged within the sleeve and welded to it. This makes it possible to obtain a very stable fixation which at the same time has a sealing function.

In a further advantageous embodiment of the present invention, the sealing element has a cylindrical recess on one face so that an annular marginal area is formed, the weld preferably running in this marginal area.

DETAILED DESCRIPTION

A lambda probe of the planar type is a cylindrical, oblong unit having a measuring side and a contact/reference air side, the lambda probe including, among other things, a housing containing a sensor element and a sleeve attached to a long side of the housing. A sealing device is provided on the end of the sleeve opposite the housing in such a way that a closed space serving as a reference air chamber is formed in the interior of the sleeve.

One end of the oblong sensor element penetrates into this reference air chamber while the other end terminates in a space defined by a cap provided with openings. When the lambda probe is operated, this space is placed in the exhaust air path so that the section of the sensor element lying in this space comes into contact with the exhaust air to be measured.

At its reference-air-side end, the sensor element is provided with electrical contacts which are led to the outside through the sealing device.

Since such lambda probes are generally well-known, a detailed description of their structure and mode of operation will be omitted. Only the sealing device according to the present invention will be described below based on the reference air side part 1 of a lambda probe represented in FIGS. 1 and 2.

Figure 1:
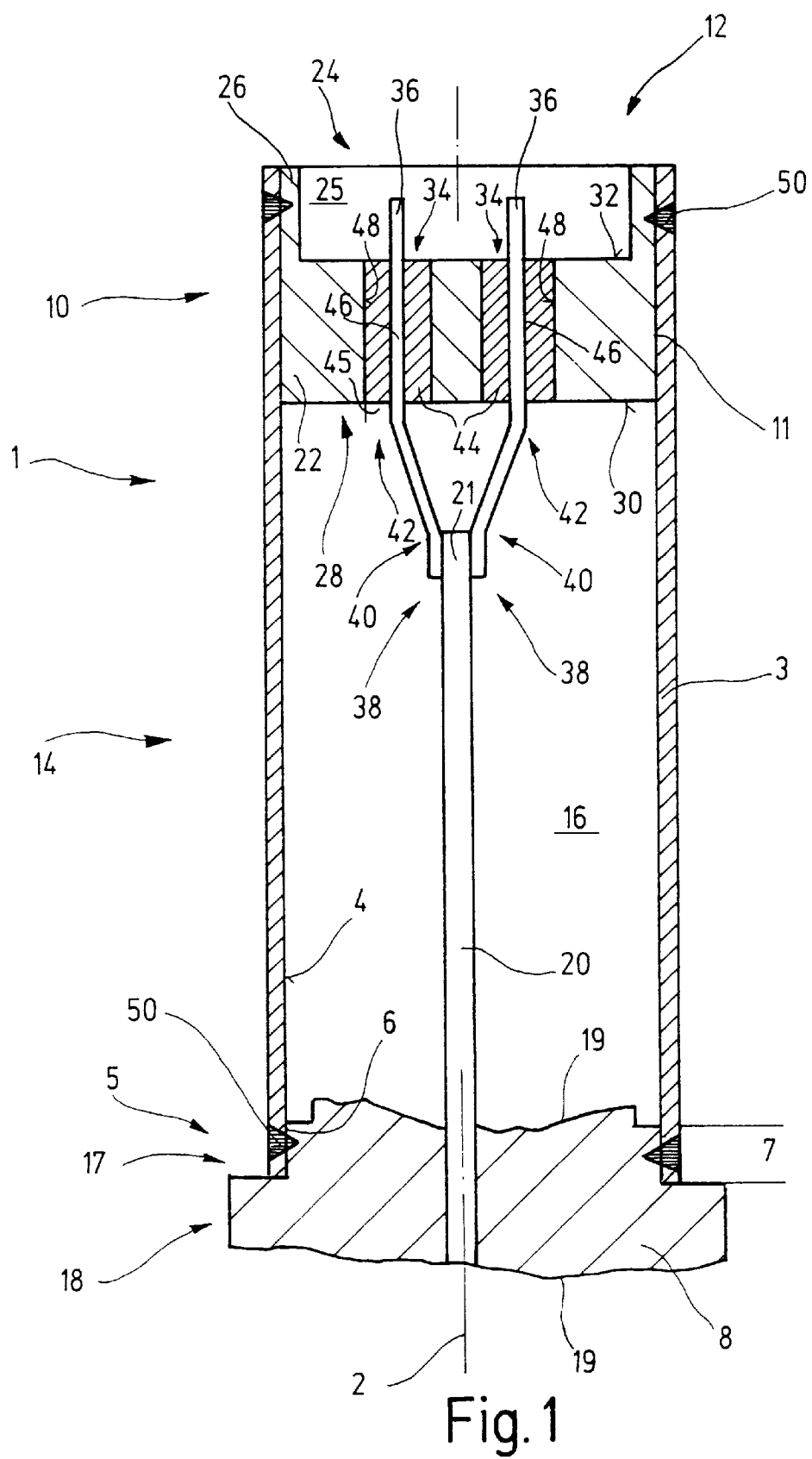
FIG. 1 shows a cut-off schematic representation in longitudinal section of an exemplary embodiment of a sealing device according to the present invention for a lambda probe of the planar type.

FIG. 1 shows a tubular, cylindrical sleeve 3 cut to length at both ends perpendicular to its central axis 2, the sleeve 3 containing various elements. In contact with inside wall 4 of sleeve 3, an initial, short end region 5 of sleeve 3 surrounds the circumference 6 of a cylindrical section 7 of a housing 8 of the lambda probe. In this manner, the bottom of sleeve 3 is closed by housing 8. The opposite second, longer end region 10 of sleeve 3 completely surrounds a cylindrical lateral surface 11 of a sealing device 12 which is inserted into sleeve 3 and closes its upper end.

Sleeve 3 which is closed at one end by housing 8 and at the opposite end by sealing device 12 thus has a sealed chamber, the reference air chamber 16, in its center region 14.

Via a step 17, housing 8 continues into a non-enclosed region 18, the larger diameter of which in comparison to the diameter of the enclosed cylindrical section 7 is capable of having flat surfaces for a wrench, which are not illustrated. It is possible to place a screw-in tool, for instance, on them in order to be able to screw the lambda sensor into an exhaust air path.

For the sake of better comprehensibility, housing 8 is shown cut off (cut-off lines 19). For this reason, also only the elements which are in direct relationship with the present invention are shown in the drawings.

A sensor element 20 is arranged centrally along center line 2, the sensor element 20 extending nearly over the entire length of the lambda probe. It is held so as to be centered in housing 8—against which it is sealed—by a washer, which is not shown, and penetrates into reference air chamber 16. Sensor element 20 terminates in an upper end 21 shortly before sealing device 12.

Sealing device 12 includes a sealing element 22 which has a cylindrical recess 25 on the face 24 facing away from reference air chamber 16, the diameter of the recess 25 being smaller than the outside diameter of sealing element 22. Thus, an annular wall region 26 is formed on sealing element 22, the annular wall region 26 changing into a cylindrical region 28, the bottom face 30 of which limits reference air chamber 16 in an upward direction. The upper face 32 of cylindrical region 28 is at the same time the bottom surface of recess 25. In the exemplary embodiment according to FIG. 1, the two faces 30 and 32 of sealing element 22 are parallel to each other and perpendicular to center line 2.

Region 28 lying between faces 30 and 32 is penetrated by two openings 34 running axially, each of which is penetrated by a contact 36.

Instead of the two openings 34 shown, there exists the possibility of providing one large opening through which the contacts 36 (at least two) are passed together at a distance from each other. It is also possible to provide more than two, for instance five, openings 34, to each of which one or several contacts 36 can be assigned. Moreover, the cross-sectional form of the openings 34 can deviate from the circular form.

Contacts 36 are fixed to end 21 of sensor element 20 in any desired manner using connections 38. Connection 38 may be, for instance, a soldered, a clamped, a welded, a plug-in or also a snap connection. It is important in this context that a durable, heat resistant electrical connection is assured. In this case, each of contacts 36 is double bent. The first offset 40, immediately after connection 38 allows contacts 36 to diverge via an angle (here approximately 40°). The second offset 42—located immediately before sealing device 12—again brings the two contacts 36 into parallel, axial alignment in which they centrally penetrate cylindrical openings 34 of sealing element 22. In their further progress, contacts 36 emerge vertically from openings 34 in an upward direction and consequently penetrate into recess 25. At this point, contacts 36 terminate. Recess 25 can receive a plug-in connection or the like which is not shown here and which can be electrically coupled with the ends of contacts 36 in order to produce a connection to an attached data transmission line.

For the purpose of sealing reference air chamber 16, for the fixation of contacts 36, and to insulate contacts 36 from sealing element 22, glass seals 44 are placed into openings 34, the glass seals surrounding longitudinal sections 46 of contacts 36 located within openings 34 in the form of a jacket. In this context, it is important that contacts 36 do not contact sealing element 22 at any point. For that reason, contacts 36 are arranged at an adequate distance to walls 48 of openings 34. This makes it clear that the layer thickness 45 of insulating glass seals 44 must not fall below a certain minimum size, since otherwise their mechanical and/or thermal stability is not assured. For this purpose, the inside diameter of openings 34 is matched to the thickness of longitudinal sections 46 of contacts 36. In order to ensure a sufficiently close contact of glass seals 44 with walls 48 and longitudinal sections 46, the cited elements have adequate surface properties, in particular roughness.

Glass seals 44 may also be modified glass. The properties of modified glass may thus vary from the properties typical of glass. Thus, for instance, the hardness or the brittleness and/or the elasticity and/or the thermal/elongation characteristics may be selectively influenced by additives.

It should be additionally pointed out that the shape of contacts 36 between their connection 38 to sensor element 20 and longitudinal sections 46 may deviate from the described double bent form of the exemplary embodiment according to FIG. 1.

Sleeve 3 which is comprised of metal is welded for the purpose of sealing reference chamber 16 and for its fixation to sealing element 22, which is also made of metal, and housing 8. Preferably, laser beam circumferential welding is used for this purpose. Annular weld 50 on the end of sleeve 3 facing sealing device 12 runs in the area of annular wall region 26. It ensures a solid connection between sealing device 12 and sleeve 3. At the bottom end of sleeve 3, an additional weld 50 also runs in an annular form in the end region 5 of the sleeve. Additional weld 50 seals sleeve 3 from housing 8.

As a whole it is made evident, that sleeve 3, which is tightly sealed at one end by housing 8 and by sealing device 12 at its opposite end, creates a space which is distinguished by a heat-resistant seal. This space, created in particular by the heat-resistant sealing device 12, which is utilized as a hermetically sealed reference air chamber 16, is essentially only in contact with the environment via contacts 36 and sensor element 20.

Furthermore, sealing device 12 increases the mechanical stability of the reference-air-side part 1 of the lambda probe.

Figure 2:
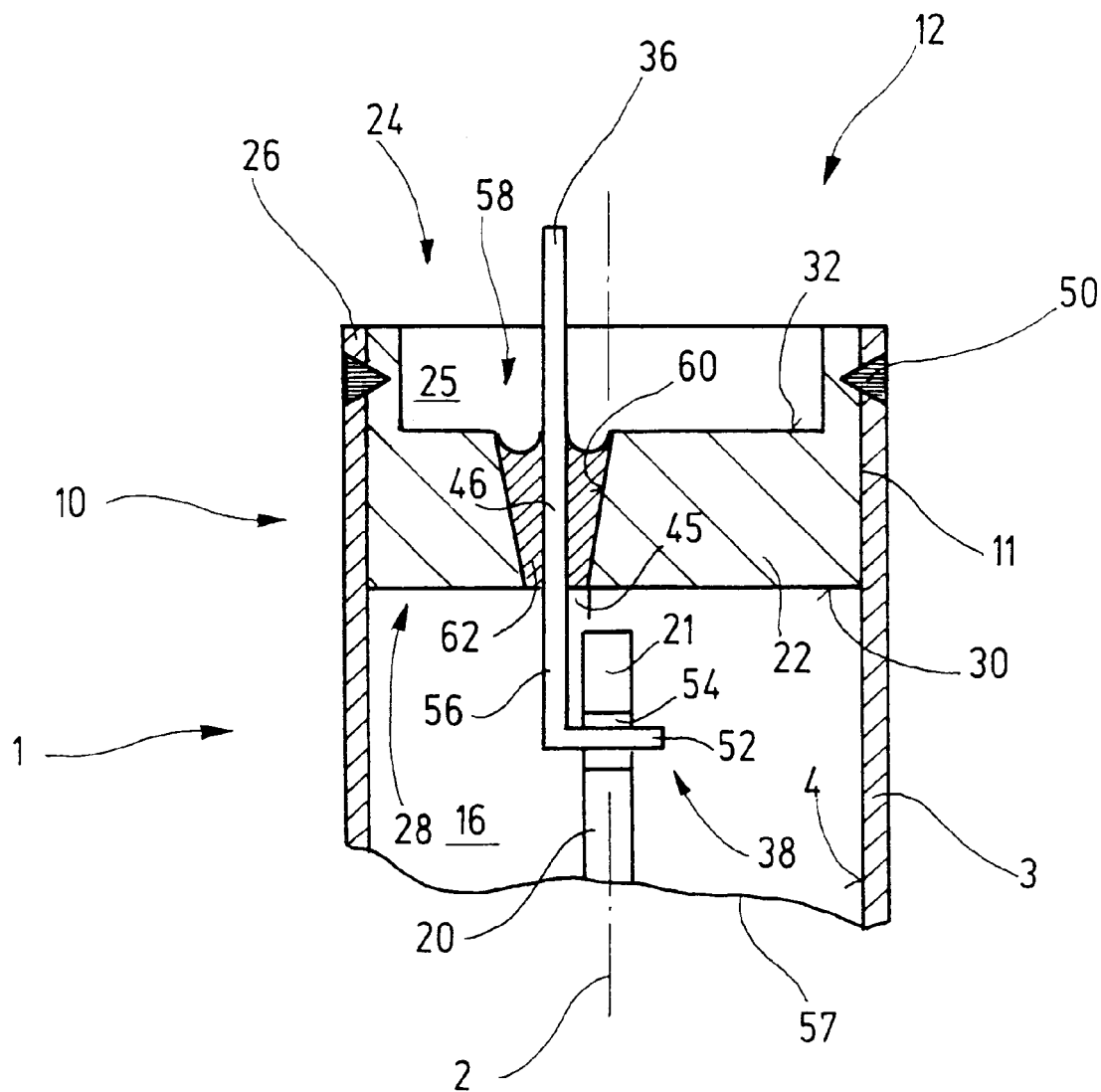
FIG. 2 shows a schematic representation of a further exemplary embodiment of the present invention.

FIG. 2 shows an additional exemplary embodiment of a sealing device 12 installed in a lambda probe.

The design of the sealing device 12 in FIG. 2 is to a large extent consistent with the one described in FIG. 1. Identical elements are provided with the same drawing references and are therefore not described once more. Basically, the statements made in connection with FIG. 1 are also applicable here. Only the differences with respect to the representation shown in FIG. 1 will now be described in detail.

Contact 36 is formed in the shape of an 'L' and has two legs of different length. Short leg 52 located entirely within reference air chamber 16 penetrates an opening 54 of sensor element 20 horizontally in order to achieve an electrical connection 38 with sensor element 20. Leg 52 may be soldered to sensor element 20. This electrical connection 38 can, for instance, be made as a welded, crimped, snap or plug-in connection. Long leg 56 of contact 36 runs vertically upwards in an axial direction. It penetrates a funnel-shaped opening 58 of sealing element 22, continues through recess 25 and terminates above face 24 of sealing element 22. The diameter of funnel-shaped opening 58 diminishes toward housing 8. Wall 60 of opening 58 thus proceeds at an angle to center line 2, which is approximately 10° in this case. Wall 60 may, however, deviate from this number of degrees.

Glass seal 62 is solidified corresponding to the funnel shape of opening 58. Glass seal 62 completely surrounds longitudinal section 46 of contact 36 which penetrates the center of opening 58 and insulates longitudinal section 46 against sealing element 22. The central arrangement of longitudinal section 46 in opening 58 is also readily apparent here via which an adequately strong vitrification on all sides is assured.

Cutoff line 57 in central region 14 of sleeve 3 limits the representation in a downward direction.

A heat-resistant, long-lasting seal of reference air chamber 16 is present with this embodiment also. Of course, a hermetic design of reference air chamber 16 requires, in addition to the sealing of the end of sleeve 3 facing away from housing 8, the sealing of the end of sleeve 3 facing housing 8. In this case, suitable means of pressure equalization can be provided in order to reduce or prevent unacceptably high overpressures or underpressures which could arise in reference air chamber 16 which, in operation, is heated to approximately 500° C.

In addition to the very good thermal properties of sealing device 12, its manufacture and assembly with sleeve 3, sensor element 20, and housing 8 of the lambda probe is very simple.

The manufacture of reference-air-side sealing device 12, its attachment to sleeve 3 and to housing 8 of the lambda probe as well as the electrical bonding of sensor element 20 will be described below. The sequence of the individual production steps can be switched.

Initially, the cylindrical sealing element 22 made of metal, including cylindrical recess 25, is produced, for instance by turning, by a casting process (die casting) or by hot or cold forming. Openings 34, 58 are then put in place by boring, for instance. Subsequently, contacts 36 are fed through openings 34, 58 and longitudinal sections 46 of contacts 36 are then completely enclosed on all sides with glass (glass seal 44, 62). This produces the seal between sealing element 22 and contacts 36 as well as their fixation to sealing element 22. For the vitrification of longitudinal sections 46 of contacts 36, either a suitable glass seal 44, 62 is poured into the annular clearance between longitudinal section 46 and wall 48, 60 of openings 34, 58 or a solder glass is inserted there, which is then melted by subsequent heating. After cooling or solidification/setting of glass seal 44, 62, contacts 36 are connected with sensor element 20 via connection 38. This can be carried out, for instance as soldered, welded, crimped, snap or plug-in connection. After completion of electrical connection 38, the metallic, tubular sleeve 3 is fitted on so that sleeve 3 completely surrounds a part of housing 8 which is made of metal and sealing element 22. In a final production step, the reference-air-side end of sleeve 3 is welded to sealing element 22 and the opposite end of sleeve 3 is welded to housing 8, particularly by laser beam circumferential welding.

The manufacture and assembly of the reference-air-side part of the lambda probe according to FIG. 2 is now carried out as follows.

In an initial step, contact 36 is connected with sensor element 20 of the lambda probe. After completion of electrical connection 38, sleeve 3 is fitted onto cylindrical section 7 of housing 8 and welded to cylindrical section 7, particularly by laser beam circumferential welding (weld 50). Subsequently, sealing element 22 is inserted into the long end region 10 of sleeve 3 so that contact 36 penetrates opening 58 in sealing element 22. Now the annular wall area 26 of sleeve 3 is welded to sealing element 22. Both welds 50 can also be carried out—in direct succession—after the insertion of sealing element 22 into sleeve 3.

It is also possible to initially insert sealing element 22 into the long end region 10 of sleeve 3, to weld the two parts together and then to fit them with the short end region 5 of sleeve 3 onto cylindrical section 7 of housing 8. In this case, contact 36 connected previously with sensor element 20 must be fed through opening 58 in sealing element 22. Subsequently, sleeve 3 is joined to housing 8 of the lambda probe via weld 50.

Here also, the two welds 50 can be completed in direct succession, namely only after the combination of sealing element 22 and sleeve 3, obtained by a snug fit for instance, has been fitted onto housing 8. Independently of the sequence of the individual production steps, longitudinal section 46 of contact 36 is sealed by glass as described.

With the described method, a simple and consequently cost-effective manufacture of the reference-air-side of a lambda probe is made available.

What is claimed is:

1. An engine exhaust gas measuring sensor, comprising:
    a metallic sleeve having a first end for connection to a housing;
    a sealing device coupled a second end of the metallic sleeve facing away from the housing, the sealing device including:
        a metallic sealing element,
        at least one oblong contact penetrating at least one opening of the metallic sealing element extending along a longitudinal direction of the metallic sealing element, and
        at least one glass seal arranged in the at least one opening and forming a jacket surrounding a longitudinal section of the at least one oblong contact arranged within the at least one opening, wherein the at least one glass seal is positioned where the at least one oblong contact penetrates the at least one glass seal; and
    a sensor element arranged in the housing and being electrically coupled to the at least one oblong contact.

2. The gas measuring sensor according to claim 1, wherein the metallic sealing element is arranged within the metallic sleeve and is coupled to the metallic sleeve by a weld running in an annular shape and serving as a seal and as a fixation device.

3. The gas measuring sensor according to claim 2, wherein the metallic sealing element includes a face having a cylindrical recess provided therein in order to form an annular marginal region.

4. The gas measuring sensor according to claim 3, wherein the weld runs in an area of the annular marginal region.

5. The gas measuring sensor according to claim 1, wherein the at least one opening is cylindrical.

6. The gas measuring sensor according to claim 1, wherein the at least one opening is formed according to a shape of a funnel having a diameter that diminishes along a direction toward the housing.

7. The gas measuring sensor according to claim 1, wherein:
    the at least one opening includes a plurality of openings traversing the metallic sealing element, and
    the at least one oblong contact includes a plurality of contacts, each one of the plurality of contacts penetrating a corresponding one of the plurality of openings.

8. A method for manufacturing a sealing device for an engine exhaust gas sensor having a metallic sleeve and a sensor element therein, comprising the steps of:
    inserting a contact through an opening of a metallic sealing element;
    arranging a glass seal in the opening so that the glass seal serves as a jacket surrounding a longitudinal section of the contact, wherein the glass seal is arranged so that the contact penetrates the glass seal; and
    cooling the glass seal in one of a solidifying operation and a setting operation.

9. The method according to claim 8, wherein the step of arranging the glass seal includes the steps of:
    introducing a solder glass into the opening, and after the solder glass is placed in the opening, fluidizing the solder glass by performing a heating operation.

10. The method according to claim 8, further comprising the steps of:
   coupling the contact to a sensor element of a lambda probe;
   fitting a sleeve onto a housing and the sealing element in order to completely enclose a cylindrical section of the housing and the sealing element within the sleeve; and
   welding the sleeve to the sealing element and to the housing.

11. The method according to claim 8, wherein the opening is formed according to a shape of a funnel having a diameter that diminishes along a direction toward a housing.

12. An engine exhaust gas measuring sensor, comprising:
   a metallic sleeve having a first end for connection to a housing;
   a sealing device coupled a second end of the metallic sleeve facing away from the housing, the sealing device including:
      a metallic sealing element,
      at least one oblong contact penetrating at least one opening of the metallic sealing element extending along a longitudinal direction of the metallic sealing element, wherein the at least one opening is formed according to a shape of a funnel having a diameter that diminishes along a direction toward the housing, and
      at least one glass seal arranged in the at least one opening and forming a jacket surrounding a longitudinal section of the at least one oblong contact arranged within the at least one opening; and
   a sensor element arranged in the housing and being electrically coupled to the at least one oblong contact.

* * * * *